US009629981B2

(12) United States Patent
Thungana et al.

(10) Patent No.: US 9,629,981 B2
(45) Date of Patent: Apr. 25, 2017

(54) DRAINAGE CATHETER

(71) Applicant: Dolcera Information Technology Services Private Limited, Hyderabad (IN)

(72) Inventors: Praveen Thungana, Hyderabad (IN); Abhinandan Bhattacharya, Hyderabad (IN); Lakshmikant Goenka, Hyderabad (IN); Sumair Riyaz Hakaim, Hyderabad (IN); Anil Sharma, Thane (IN)

(73) Assignee: DOLCERA INFORMATION TECHNOLOGY SERVICES PRIVATE LIMITED (IN)

( * ) Notice: Subject to any disclaimer, the term of this patent is extended or adjusted under 35 U.S.C. 154(b) by 0 days.

(21) Appl. No.: 14/265,596

(22) Filed: Apr. 30, 2014

(65) Prior Publication Data

US 2015/0165160 A1    Jun. 18, 2015

(30) Foreign Application Priority Data

Dec. 13, 2013 (IN) .......................... 5810/CHE/2013

(51) Int. Cl.
*A61M 25/01* (2006.01)
*A61M 25/00* (2006.01)

(52) U.S. Cl.
CPC ..... *A61M 25/0108* (2013.01); *A61M 25/0068* (2013.01)

(58) Field of Classification Search
CPC ........ A61M 25/0026; A61M 2025/006; A61M 25/0111; A61M 25/001; A61M 25/0067; A61M 25/0068; A61M 25/0069

USPC ................... 604/527, 103.01, 362
See application file for complete search history.

(56) References Cited

U.S. PATENT DOCUMENTS

| 5,011,469 A | * | 4/1991 | Buckberg ............ A61M 1/3621 |
| | | | 604/508 |
| 5,053,004 A | * | 10/1991 | Markel et al. ................... 604/43 |
| 5,081,997 A | | 1/1992 | Bosley, Jr. et al. |
| 5,289,831 A | | 3/1994 | Bosley |

(Continued)

FOREIGN PATENT DOCUMENTS

| WO | 2013122592 A1 | 8/2013 |
| WO | 2013183279 A1 | 12/2013 |

OTHER PUBLICATIONS

I Flow, A Kimberly-Clark Health Care Company, "ON-Q : Seeing is Believing with the Total Nerve Block Solution" Retrieved from: myON-Q.com, Retrieved on: Nov. 2013 (4 pages total).

(Continued)

*Primary Examiner* — Imani Hayman
*Assistant Examiner* — Hamza Darb
(74) *Attorney, Agent, or Firm* — Mark D. Wieczorek; Mayer & Williams PC

(57) ABSTRACT

A multipurpose catheter includes an un-tapered portion and a tapered portion, the latter being disposed distally of the former. The catheter has an arrangement of echo reflective features over at least a portion of the tapered portion. The echo reflective features may be echo reflective solely due to their shape, or may be made of radio opaque materials, and thus may provide a degree of echogenicity not only due to their material but also due to the reflectivity of their shape.

13 Claims, 3 Drawing Sheets

(56) References Cited

U.S. PATENT DOCUMENTS

| | | | |
|---|---|---|---|
| 5,759,154 A * | 6/1998 | Hoyns | A61B 8/0833 29/DIG. 16 |
| 6,527,752 B1 | 3/2003 | Bosley, Jr. et al. | |
| 6,860,856 B2 | 3/2005 | Ward et al. | |
| 6,863,654 B2 | 3/2005 | Zappala et al. | |
| 8,430,863 B2 | 4/2013 | Webler | |
| 9,254,146 B2 | 2/2016 | Massengale et al. | |
| 2004/0073158 A1 * | 4/2004 | Shah et al. | 604/19 |
| 2005/0096642 A1 * | 5/2005 | Appling | A61B 18/24 606/15 |
| 2006/0247530 A1 | 11/2006 | Hardin, Jr. et al. | |
| 2008/0097213 A1 * | 4/2008 | Carlson et al. | 600/458 |
| 2009/0005774 A1 | 1/2009 | Fernald | |
| 2009/0326560 A1 | 12/2009 | Lampropoulos et al. | |
| 2010/0274178 A1 * | 10/2010 | LePivert | 604/21 |
| 2010/0317963 A1 | 12/2010 | Clancy | |
| 2011/0046619 A1 * | 2/2011 | Ducharme | A61B 18/1477 606/41 |
| 2011/0224538 A1 * | 9/2011 | Linares | A61B 8/0841 600/424 |
| 2012/0095404 A1 | 4/2012 | Massengale et al. | |
| 2012/0265055 A1 | 10/2012 | Melsheimer et al. | |
| 2013/0053825 A1 * | 2/2013 | Moulton | A61M 25/0074 604/523 |
| 2013/0190609 A1 | 7/2013 | Fischer, Jr. | |

OTHER PUBLICATIONS

B Braun Sharing Expertise, "Contiplex® S Ultra & Contiplex® Tuohy Ultra" Retrieved from: http://www.bbraun.com/cps/rde/xchg/bbraun-com/hs.xsl/11746.html, Retrieved Nov. 2013 (3 pages total).

Rocketmedical, "Rocket Echo Cath: Ultrasound Embryo Transfer Catheter Sets" 2013, Retrieved from: www.rocketmedical.com, Retrieved Nov. 2013 (1 page total).

Holzgreve, et al., "Chorionic villi sampling with an echogenic catheter: experiences of the first 500 cases" J. Perinat. Med. (15) 1987, pp. 244-250 (7 pages total).

Pajunk "SonoSystem: The complete system for ultrasound guided nerve blocks" Retrieved from: www.pajunkadvantage.com/pdf/SonoSystem_GB.pdf, Retrieved Nov. 2013 (16 pages total).

* cited by examiner

DRAINAGE CATHETER

CROSS-REFERENCE TO RELATED APPLICATIONS

This application claims benefit and priority to Indian Patent Application No. 5810/CHE/2013, filed Dec. 13, 2013, incorporated herein in its entirety.

BACKGROUND

In their bare form, drainage catheters are known and may be applied in a number of scenarios. For example, drainage catheters may be employed to drain urine from the kidney or bladder, to collect fluid from, e.g., an abscess, a cavity, or the like. Catheters are also known for the administration of intravenous fluids, as well as anesthetics, contrast media, and the like.

Advancements in drainage catheters have also been seen, e.g., in the area of increasing visibility of the catheter. For example, in US PGP 2010/0317963, a catheter is shown having a dimpled region to enhance the echogenecity of a region, and further discloses ribs, ridges, etc., for the same purpose. In U.S. Pat. No. 5,289,831, spherical indentations 905 are employed to scatter a sonic beam to produce a component of an image. In U.S. Pat. No. 6,527,752, indentations are also used as ultrasonically-reflective features. In U.S. Pat. No. 5,081,997, partially-spherical indentations are also employed to scatter sonic beams. In US PGP 2008/0097213, various components are disclosed for enhancing detection under ultrasound or MRI. In US PGP 2012/0095404, various components are described which are alleged to enhance echogenicity. In U.S. Pat. No. 6,860,856, ways of increasing the ultrasonic visibility of a needle are disclosed, including the formation of dimples or using etching on the surface. In US PGP 2013/0190609, structures for enhancing echogenicity are disclosed, including dimpling in various patterns, including in stripes. In US PGP 2006/0247530, a catheter is disclosed having a lumen and an echogenic surface. In another implementation, the I-FLOW® products from Kimberly-Clark in some cases incorporate micro laser etching to improve reflection. Certain products from Braun include needles enhanced with laser-crafted ultrasound reflectors. Certain products from Pajunk® are alleged to provide 100% reflection under ultrasound monitoring. Finally, in a paper entitled "Chorionic Villi Sampling With An Echogenic Catheter: Experiences Of The First 500 Cases", Wolfgang Holzgreve and Peter Minya disclose the use of an echo reflecting stripe in the wall of a catheter.

However, all of the above are associated with various disadvantages. In particular, while each includes certain ways to enhance visibility, each still relies significantly on the skill of the physician or other medical professional to deploy the catheter in a proper position and use the same.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Implementations of systems and methods according to present principles provide an improved drainage catheter with enhanced imaging capabilities. Certain implementations provide a catheter which can be deployed by a physician under ultrasound but which does not require significant physician deployment skill. Certain implementations of systems and methods according to present principles allow the catheter to be delivered and used in real time under imaging, in contrast to prior systems which generally are not for use in real time.

DETAILED DESCRIPTION

As may be seen in the figures, the catheter generally includes an un-tapered portion 12 and a tapered portion 14, 16, 18, or 22, the latter being disposed distally of the former. The tapered portion may be, e.g., 150 mm, and the untapered portion may be, e.g., 75 mm, though of course these are purely exemplary. Each has a generally cylindrical elongated shape. Various embodiments include a plurality of holes 28$i$ defined therein for accomplishing the goal of drainage as described above. Such holes may generally have diameters of from 0.1 mm to 15 mm, and the number of such holes may be from 2 to 200. In the figures, the holes are generally on the tapered portion, but in certain implementations the same may also be disposed on the un-tapered portion (not shown).

Figure 1:
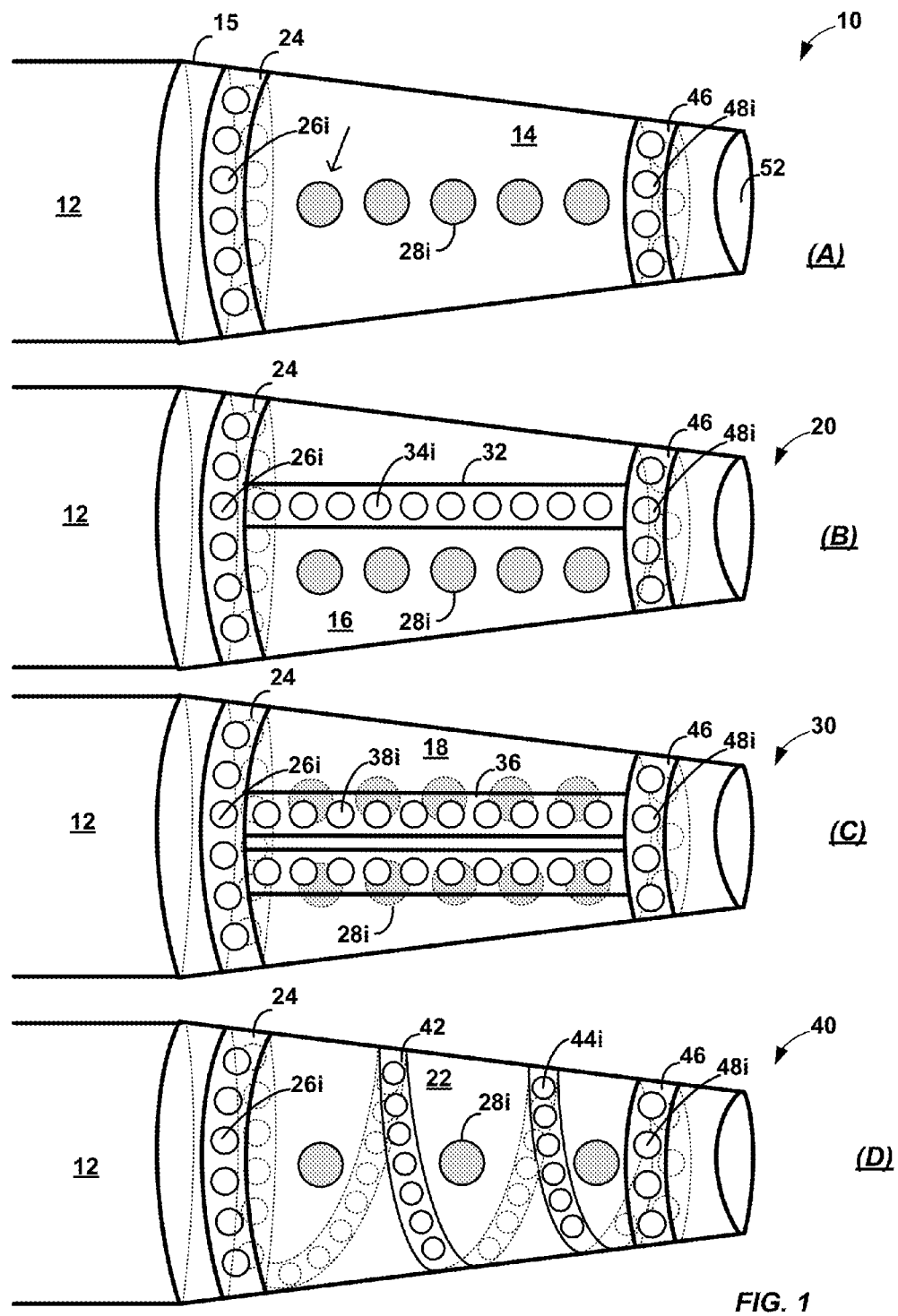
FIGS. 1(A)-1(D) illustrate various embodiments of a drainage catheter according to present principles.

In FIG. 1(A), it may be seen that the device 10 includes a tapered portion including two frustal annuli 24 and 46, one at a distal tip 52 of the distal end and the other at a proximal end 15 of the tapered portion, near the junction with the un-tapered portion. The two frustal annuli include portions 26$i$, 48$i$ that are echo-reflective under ultrasound. For example, the annuli may include portions having echo reflective features such as dimples, depressions, or bumps, in various arrangements, where the arrangement is selected to enhance visualization with respect to a given anatomy. Using an imaging modality, e.g., ultrasound, a physician viewing the tapered portion would see two annuli of different radius. The physician would know that the distal tip would be near or adjacent the annulus with the smaller radius. Assuming the physician inspected the catheter prior to delivery, and knew how far the distal tip was from the smaller annulus, the location and orientation of the catheter distal end may become substantially known. In any given implementation, the choice of echo reflective feature arrangement, as well as the choice of arrangement and sizing of the drainage holes, may be selected according to a given anatomy as will be known to one of ordinary skill in the art given this disclosure.

Various examples will be seen, for example, in FIG. 1(B), a device 20 includes that the two annuli are joined by a straight axial line 32 of echo reflective features 34$i$ such as depressions, dimples, or bumps. In this system, not only does the line give a greater indication of the orientation, delivering additional visual information to the physician, but the axial straight line can also disambiguate the location of the distal end about an azimuthal angle, i.e., the angle of rotation of the catheter shaft can become known. In the device 30 of FIG. 1(C), a double line 36 of echo reflective features 38i are illustrated, with drainage holes on the opposite side of the tapered portion. It will be clear that the echo reflective features may be on the same side as the drainage holes, the opposite side, or in a number of different configurations. In the device 40 of FIG. 1(D), a helical arrangement 42 of echo reflective features 44i is illustrated between the two annuli. A helical arrangement may be particularly convenient to visualize. However, it is noted that in all implementations, the position and orientation of the distal end of the drainage catheter may be substantially known in an unambiguous fashion under the various imaging modalities.

It is further noted that while two annuli have been illustrated in each implementation according to present principles, there is no need for this number: a greater or lesser number of annuli may be employed, including no annuli, e.g., only the helical or straight-line echo reflective features may be employed.

The echo reflective features may be echo reflective solely due to their shape, or (alternatively or in addition to) may be made of radio opaque materials, and thus may provide a degree of echogenicity not only due to their material but also due to the reflectivity of their shape. While dimples, depressions, or bumps have been described, in some implementations r dimples have been found particularly effective. In the case of echo reflective features being bumps, depressions, or dimples, the shape may be specified to further enhance echogenicity, and particularly effective shapes include hemispheres or portions of hemispheres. In one implementation, a dimple diameter may be 0.5 to 2 mm, e.g., 1 mm.

The arrangement or coordination of the echo reflective features and the drainage holes may provide a particularly effective system.

The overall shape of the catheter can vary, although a proximal portion is generally in an elongated straight (though flexible) shape. A distal end can be straight or can take on other shapes according to the requirements of the anatomy in which the catheter is placed, as well as the needs for drainage. One type of shape the distal end may take on is a pigtail shape. In such an implementation, the catheter and the distal end are often in a straight configuration during installation before deployment. The deployed configuration may be a pigtail shape or the like, as configurable by control wires operated from the handle of the catheter, which can transform the distal end and/or tip of the catheter to a pigtail shape in known fashion.

Variations will be apparent. For example, while bumps and depressions have been disclosed, arrangements according to present principles may include provision of the echo reflective features within the material of the tapered portion (or the un-tapered portion), or the same may be provided a separate band, strip, or ribbon that is molded onto the tapered and/or on tapered portion. Besides use of dimples, bumps, or depressions, the same may incorporate glass beads or flakes or other reflective matter to enhance echogenicity.

Figure 3:
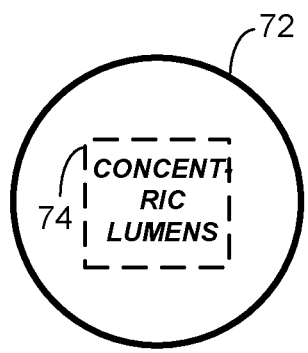
FIG. 3 illustrates an embodiment of a drainage catheter according to present principles having concentric lumens.
Figure 4:
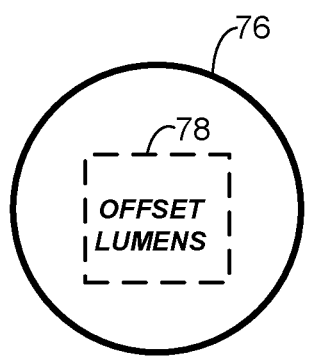
FIG. 4 illustrates an embodiment of a drainage catheter according to present principles having offset lumens.

One or more lumens may be defined within the body of the catheter, such as a main lumen and a lumen for drug delivery or delivery of contrast media or medical devices or the like (in which case a stopcock or other connector may be positioned at a proximal end of the lumen). Such lumens may also be useful for delivering the catheter over a guide wire. In one implementation, shown in FIG. 3, a main lumen 72 is concentric with a delivery lumen 74. In another implementation, shown in FIG. 4, a main lumen 76 is offset from a delivery lumen 78.

The preferred embodiment of the invention is useful for drainage catheters. Other embodiments of the invention can be used in other types of catheters, e.g., coronary catheters, urological catheters, diagnostic catheters, etc. The invention can also be used in other medical devices such as needles, cannula, or any other tubular invasive medical device inserted with the help of imaging devices, particularly ultrasound.

Figure 2:
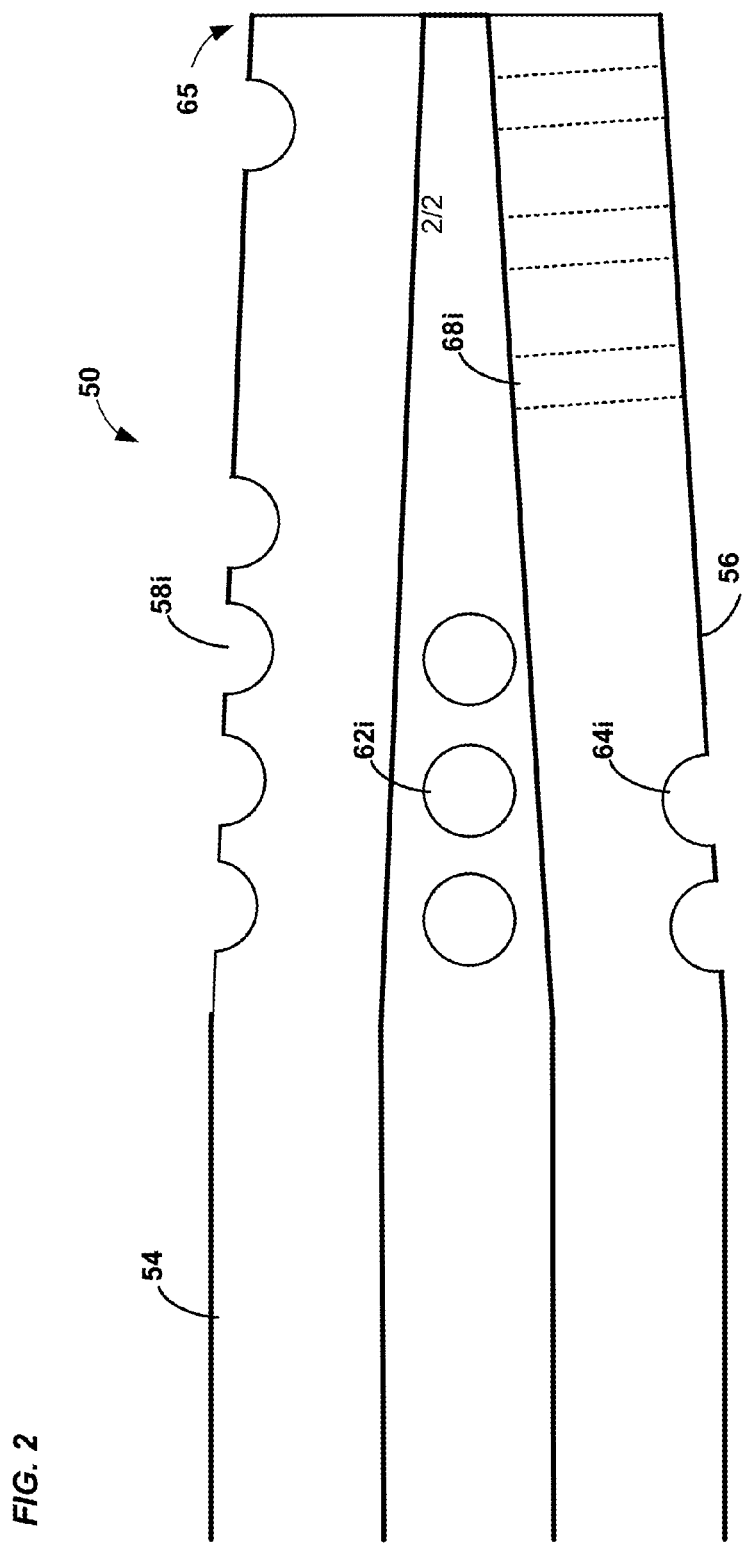
FIG. 2 illustrates another embodiment of a drainage catheter according to present principles.

A particular implementation according to present principles is described in FIG. 2. In this implementation 50, an untapered portion 54 is proximal of a tapered portion 56, and drainage holes 68i, having a diameter of, e.g., 3.5 mm, are provided at a distal tip 65 of the catheter, and in particular on the tapered portion 56, over an approximately 60 mm portion, leaving 90 mm without such holes, and dimples for echolocation 58i, 62i, and 64i are provided in a particular arrangement so as to allow disambiguation, i.e., location of the catheter distal end in both position and orientation. The dimples may have a diameter of, e.g., 1 mm. Various dimensions have been provided above. As is clear, such is a particular implementation and the values shown are purely exemplary.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A multipurpose catheter, comprising
   a. an elongated cylindrical untapered portion;
   b. an elongated cylindrical tapered portion distal of the untapered portion; and
   c. an arrangement of echo reflective features formed over the tapered portion, the arrangement comprising at least two frustal annuli joined by a straight axial line, wherein the arrangement allows disambiguation of a location of the tapered portion about an azimuthal angle, a position and an orientation when the catheter is visualized using an imaging modality, wherein the echo reflective features include one or more from the group consisting of: dimples, depressions, or bumps,
   d. wherein the untapered portion and the tapered portion define at least one lumen, and at least one hole located between the two frustal annuli and adjacent to the straight axial line, the at least one hole in fluid communication with the lumen, and
   e. wherein an imaging modality is sufficient to indicate the location and orientation of a distal end of the elongated cylindrical tapered portion using the arrangement of echo reflective features as formed by the at least two frustal annuli.

2. The catheter of claim 1, wherein the catheter is made of a material allowing echo reflective imaging.

3. The catheter of claim 1, wherein the untapered portion and the tapered portion define at least another lumen, wherein the at least one lumen is a main lumen and the at least another lumen is for delivery of a fluid.

4. The catheter of claim 3, wherein the main lumen and the at least another lumen are offset.

5. The catheter of claim 1, wherein the shape of at least one of the dimples, depressions or bumps is a hemisphere, a partial hemisphere, triangular, conical (inverted), rectangular or square.

6. The catheter of claim 1, wherein the elongated cylindrical untapered portion and the elongated cylindrical tapered portion are configured to be straight in an undeployed configuration, and at least a distal end is configured to be in a pigtail shape in a deployed configuration, and wherein the distal end has a location and orientation determinable by the imaging modality.

7. The catheter of claim 1, wherein the straight axial line is linear or double linear.

8. The catheter of claim 1, further comprising an isolated echo reflective feature on a distal tip of the tapered portion.

9. A method of draining fluid from a body of a patient, comprising inserting a catheter according to claim 1 in a patient, maneuvering a distal tip of the catheter to a desired location for drainage using the imaging modality and the arrangement of echo reflective features, and draining fluid through the hole.

10. A multipurpose catheter, comprising
   a. an elongated cylindrical untapered portion;
   b. an elongated cylindrical tapered portion distal of the untapered portion; and
   c. an arrangement of echo reflective features couplable as a band over the tapered portion, the arrangement comprising at least two frustal annuli joined by a straight axial line, wherein the arrangement allows disambiguation of a location of the tapered portion about an azimuthal angle, a position and an orientation when the catheter is visualized using an imaging modality, and wherein the arrangement of the echo reflective features on the couplable band is modifiable with respect to a given anatomy.

11. The multipurpose catheter of claim 10, wherein a plurality of drainage holes are located between the two frustal annuli, the straight axial line and the plurality of drainage holes located on opposite sides of the elongated cylindrical tapered portion.

12. The multipurpose catheter of claim 10, wherein a plurality of drainage holes located between the two frustal annuli and adjacent to the straight axial line.

13. A multipurpose catheter, comprising
   a. an elongated cylindrical untapered portion;
   b. an elongated cylindrical tapered portion distal of the untapered portion; and
   c. an arrangement of echo reflective features formed over tapered portion, the arrangement comprising at least two frustal annuli connected by a helix, wherein the arrangement allows disambiguation of a location of the tapered portion about an azimuthal angle, a position and an orientation when the catheter is visualized using an imaging modality, wherein the echo reflective features include one or more from the group consisting of: dimples, depressions, or bumps;
   d. wherein the untapered portion and the tapered portion define at least one lumen, and at least one hole located between the two frustal annuli, the at least one hole in fluid communication with the lumen, and
   e. wherein an imaging modality is sufficient to indicate the location and orientation of a distal end of the elongated cylindrical tapered portion using the arrangement of echo reflective features as formed by the at least two frustal annuli.

* * * * *